US010803976B2

United States Patent
Pillai

(10) Patent No.: US 10,803,976 B2
(45) Date of Patent: Oct. 13, 2020

(54) COLLABORATION NETWORKING TOOL

(75) Inventor: Vijay K. Pillai, Potomac Falls, VA (US)

(73) Assignee: Oracle International Corporation, Redwood Shores, CA (US)

(*) Notice: Subject to any disclaimer, the term of this patent is extended or adjusted under 35 U.S.C. 154(b) by 1396 days.

(21) Appl. No.: 13/530,185

(22) Filed: Jun. 22, 2012

(65) Prior Publication Data

US 2013/0346104 A1 Dec. 26, 2013

(51) Int. Cl.
*G16H 10/60* (2018.01)

(52) U.S. Cl.
CPC .................... *G16H 10/60* (2018.01)

(58) Field of Classification Search
None
See application file for complete search history.

(56) References Cited

U.S. PATENT DOCUMENTS

| | | | | |
|---|---|---|---|---|
| 6,463,417 | B1* | 10/2002 | Schoenberg | 705/2 |
| 8,275,850 | B2* | 9/2012 | Kohan et al. | 709/212 |
| 2004/0215981 | A1* | 10/2004 | Ricciardi et al. | 713/202 |
| 2005/0234739 | A1* | 10/2005 | Schoenberg | 705/2 |
| 2005/0236474 | A1* | 10/2005 | Onuma et al. | 235/382 |
| 2005/0267782 | A1* | 12/2005 | Zahlmann et al. | 705/3 |
| 2008/0010254 | A1* | 1/2008 | Settimi | 707/3 |
| 2009/0012816 | A1* | 1/2009 | Cookson et al. | 705/3 |
| 2010/0241595 | A1* | 9/2010 | Felsher | 705/400 |
| 2011/0258000 | A1* | 10/2011 | Green et al. | 705/3 |
| 2012/0130746 | A1 | 5/2012 | Baker | |
| 2012/0303616 | A1* | 11/2012 | Abuelsaad et al. | 707/736 |

FOREIGN PATENT DOCUMENTS

| | | |
|---|---|---|
| AU | 2012202810 | 6/2012 |
| AU | 2012202810 A1 | 7/2012 |
| EP | 2426617 A | 3/2012 |
| EP | 2426617 A1 | 3/2012 |
| EP | 2426617 | 7/2012 |
| EP | 2426617 A1 | 7/2012 |
| JP | 2002-197186 A | 7/2002 |
| JP | 2003-196386 A | 7/2003 |
| JP | 2005-100408 A | 4/2005 |
| JP | 2007-140647 A | 6/2007 |
| JP | 2007-213139 A | 8/2007 |

(Continued)

OTHER PUBLICATIONS

Quantin et al, Medical record search engines, using pseudonymised patient identity: An alternative to centralised medical records, Int. J. Med. Informatics, 80(2011), pp. e6-e11 (Year: 2011).*

(Continued)

*Primary Examiner* — Fonya M Long
*Assistant Examiner* — William G Lultschik
(74) *Attorney, Agent, or Firm* — Kraguljac Law Group, LLC

(57) ABSTRACT

Systems, methods, and other embodiments associated with are described. In one embodiment, a method includes receiving, from a provider, de-identified data that describes patients. The method includes enabling selective access to the de-identified data in the data store by seekers authorized by the provider.

7 Claims, 9 Drawing Sheets

(56) References Cited

FOREIGN PATENT DOCUMENTS

JP          2010-237811 A          10/2010
JP          2012-018539 A          1/2012

OTHER PUBLICATIONS

Patent Cooperation Treaty (PCT) International Search Report and Written Opinion in co-pending PCT International Appl. No. PCT/US2013/040065 (International Filing Date of May 8, 2013) dated Sep. 4, 2013 (14 pgs.).

Ma et al., Study on LogicSQL Database System in Security Problems, Communication Software and Networks (ICCSN), 2011 IEEE 3rd Intl. Conference on, IEEE, May 27, 2011, pp. 532-536, XP032049985, DOI: 10.1109/ICCSN.2011.6013888; ISBN: 978-1-61284-485-5.

State Intellectual Property Office of the People's Republic of China Office Action in co-pending CN application No. 201380026992.9; pp. 1-10, filing date of May 8, 2013; notification dated Aug. 18, 2016.

Japanese Patent and Trademark Office Action in co-pending JP application No. 2015-518402; pp. 1-3, filing date of Nov. 6, 2014; notification dated Dec. 6, 2016.

Japanese Patent and Trademark Office Action in co-pending JP application No. 2015-518402; pp. 1-3, filing date of Nov. 6, 2014; notification dated Aug. 22, 2017.

State Intellectual Property Office of the People's Republic of China Office Action in co-pending CN application No. 201380026992.9; pp. 1-7, filing date of May 8, 2013; notification dated Jun. 26, 2017.

IN Examination Report dated Sep. 12, 2019 for co-pending IN Application #7397/CHENP/2014; filed Oct. 7, 2014. pp. 1-6.

JP Office Action dated Nov. 6, 2018 for co-pending JP Patent Application No. 2015518402 filed Nov. 6, 2014.

Takayuki Hoshino, "Architecture for a Data Analysis Base treating Massive and Complicated Unstructured Data", Unisys Technology Review, Nihon Unisys, Ltd., Mar. 31, 2012, vol. 31, No. 4, p. 59-67.

\* cited by examiner

_US 10,803,976 B2_

COLLABORATION NETWORKING TOOL

BACKGROUND

One major challenge faced in the development of life sciences products is access to high quality clinical information to understand the feasibility of executing clinical studies, and to recruit patients for clinical studies. Patient privacy laws and the lack of incentive for health care providers to collaborate significantly limited access to patient clinical records. In many instances, doctors act as brokers between the life sciences concern (pharmaceutical/biotech and medical device companies) performing a study to find patients who meet the study's inclusion/exclusion requirements. This limits the pool of possible patients who will benefit from the latest clinical research to patients of doctors who are in communication with the life sciences concern. This also means that recruitment of patients for a clinical trial is often done by word of mouth.

To expedite collaboration between life sciences product companies and healthcare providers, some companies serve as intermediaries and buy de-identified clinical data from health care providers and sell the data to life sciences product companies. Often providers are reluctant to sell their patient data to these intermediary companies because in doing so they lose control of their data, which is a very valuable asset to them. In addition, the patient data owned by the intermediary companies is simply a snapshot of patient data at the time of the sale, meaning that it quickly becomes outdated.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. One of ordinary skill in the art will appreciate that in some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
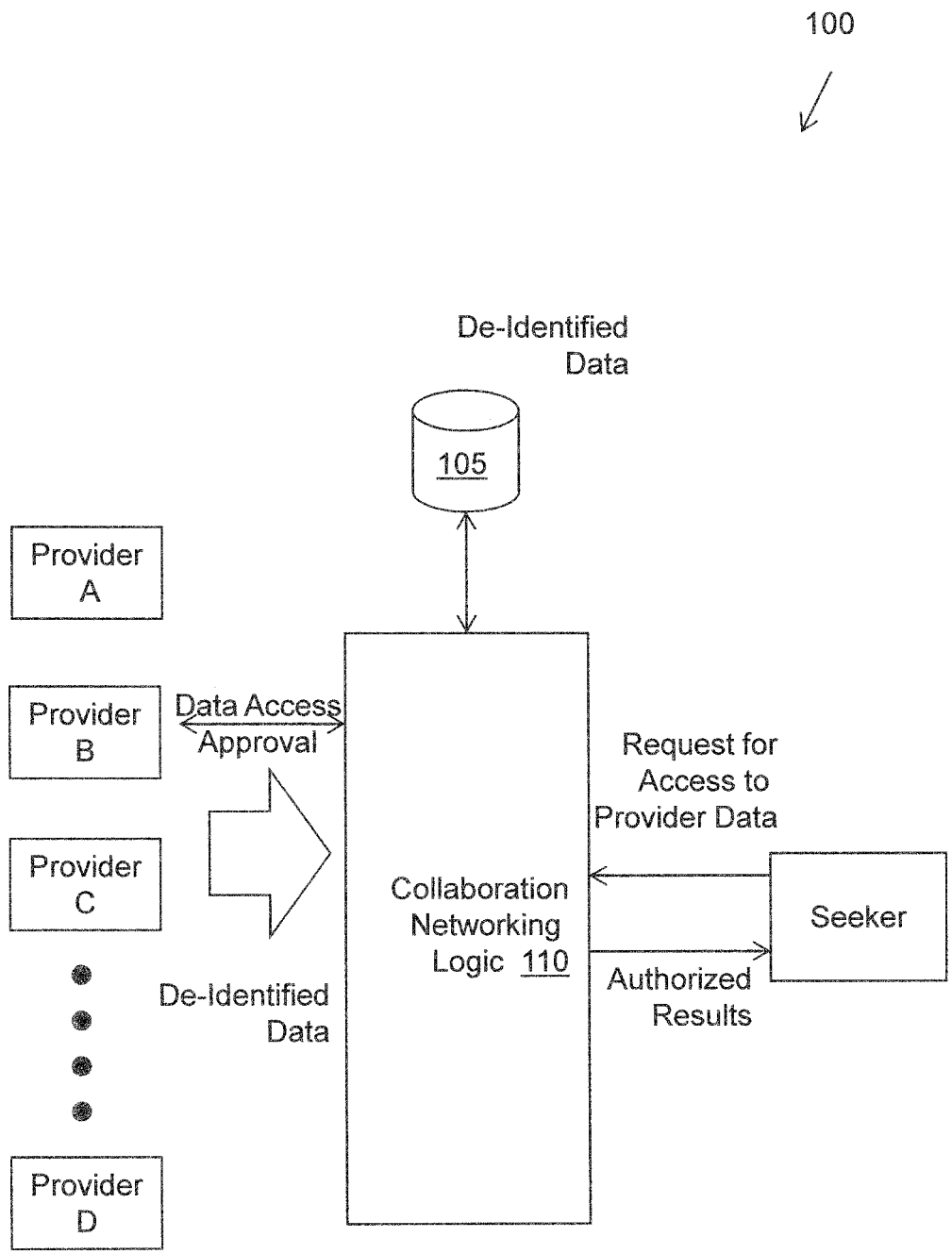
FIG. 1 illustrates one embodiment of a system associated with a collaboration networking tool.

Historically, no tool or model existed that allowed healthcare institutions safely share information (e.g., clinical data) in a meaningful manner with life sciences companies for a secondary use, such as developing new therapies, while protecting the privacy of their patients and preserving the value of the information. This sharing of clinical information between life sciences companies and healthcare institutions can be valuable in many ways. In this description, use of clinical data for locating patients for clinical trials will be the focus. However, the collaboration networking tool described herein may be employed to share information for many purposes. Some of the ways clinical data can be useful to life sciences companies are modeling and feasibility analysis of study protocols, finding the ideal candidate for clinical studies, promoting clinical research, sales, safety surveillance of drugs on the market, care management, comparative effectiveness, research, and so on.

Often, simply knowing a count of patients that meet certain protocol or criteria can be invaluable to a life sciences company. This information can help the life sciences company to modify their criteria so that it is broad enough to include a sufficient number of patients. The number of patients meeting criteria that described a condition can be used to identify a potential market for a drug that treats the condition. Knowing the number of patients meeting the criteria at various providers can assist a life sciences company to select a location for a clinical trial. The collaboration networking tool described herein enables the sharing of patient counts meeting certain criteria in a confidential manner while protecting the identities of the patients and the value of the information to the healthcare provider.

Clinical studies are an important part of the development of medical products (e.g, medical devices or pharmaceuticals). In clinical studies, a "protocol" includes selected inclusion and exclusion criteria that describe the physical characteristics of patients of interest to the study. For example, inclusion criteria may specify that the patient has a certain illness or condition while exclusion criteria may specify that the patient cannot be above a certain age. Locating a sufficient number of patients that meet the protocol criteria often proves to be an obstacle. In order to efficiently perform a clinical trial, a sufficient number of patients must be located who can interact with one of a small number of testing sites.

Historically, the process of identifying clinical study sites and recruiting patients is time consuming. In an effort to streamline these processes, Contract Research Organizations (CROs) came into existence. CROs are service organizations that are contracted by life sciences concerns to perform various aspects of medical product development, including clinical studies. Even with the benefits of scale enjoyed by CROs, the time needed to validate protocols, determine appropriate inclusion/exclusion criteria for patients, enroll a study site, and recruit patients is significant. Often, by the time the entire process has been performed, some of the patients recruited for the study are no longer suitable due to changes in their condition.

Systems and methods are described herein that provide a collaboration networking tool that hosts de-identified longitudinal information (e.g., clinical data collected over a period of time) about patients from multiple providers (e.g., health care providers). The collaboration networking tool provides access, with the provider's authorization, to this information seekers (e.g., medical products companies, CROs). Thus seekers who subscribe to the collaboration networking tool and are authorized by a provider whose data is hosted by the tool can access the data to validate a protocol (e.g., check that the criteria covers an appropriate number of patients) and/or identify patients that meet one or more criteria The collaboration networking tool serves as a host to de-identified data that describes patient characteristics that are typically the subject of protocol criteria (e.g., diagnosis, age, sex, current treatments) without including data about patients that may be used to identify a patient (e.g., name, address, treating doctor, specific geographic details). Providers may be given the opportunity to approve access to their data, allowing the provider to maintain ownership of their sensitive and valuable patient data.

Seekers may perform querying on the de-identified data hosted by the collaboration networking tool to determine if a provider has a sufficient number of patients that meet a protocol criteria. This allows seekers to pursue a collaborative relationship with a provider having enough patients meeting the protocol. That collaboration may also be performed by way of the collaboration networking tool as will be described in more detail below.

For the purposes of this description, the data hosted by the collaboration networking tool is clinical data about patients under medical treatment by health care providers. The collaboration networking tool may be used to host any type of data in which the identity of the subject of the data (e.g., patient) is to be kept confidential. For example, subjects whose data may be confidentially hosted by the collaboration networking tool include professionals who may be recruited for employment, persons seeking matchmaking services, and so on. In a broader sense, subjects may not human, but may be any entity whose data can be owned by a provider wishing to provide controlled access to that data.

While privacy restrictions prevents widespread use of electronic medical records for secondary use of clinical data, the collaboration networking tool allows health care providers to store de-identified clinical data from electronic medical records "in the cloud" (e.g., a database/data warehouse controlled by the collaboration networking tool). This creates a vast pool of patients for decision makers to be able to make accurate decisions based on high quality clinical data, speeding up the execution of studies considerably. Providers of the de-identified data benefit as well because they are giving their patients access to the latest in clinical research by providing the patients' de-identified clinical data to the collaboration networking tool.

Figure 3:
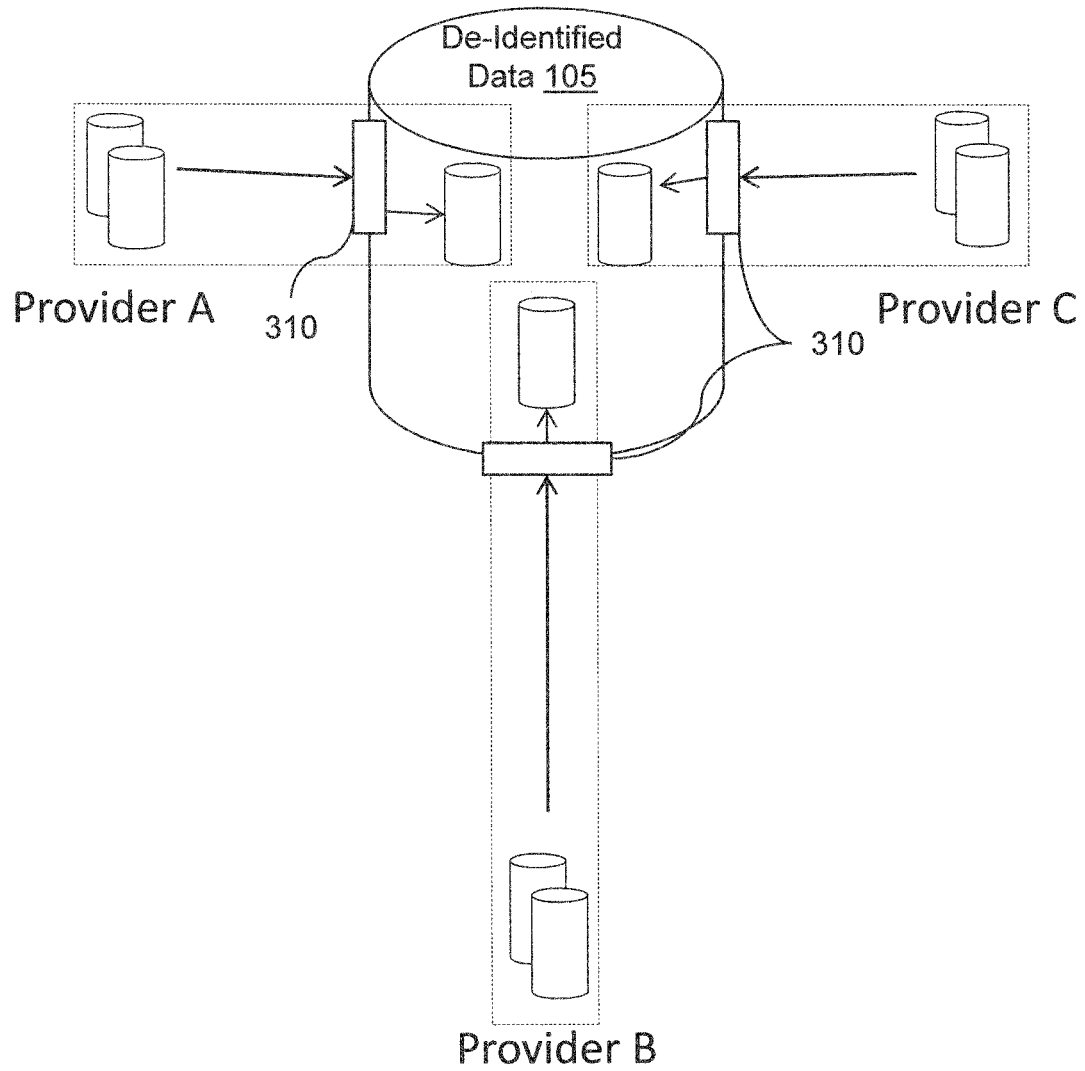
FIG. 3 illustrates one embodiment of a system associated a collaboration networking tool.

With reference to FIG. 1, one embodiment of a system 100 associated with a collaboration networking tool 110 used to host clinical data for patients is illustrated. In other embodiments, the collaboration networking tool 110 hosts data about other subjects in the manner described herein. The system 100 includes a data store 105 configured to store de-identified data (e.g., clinical data in one embodiment.) For the purposes of this description, the data describes patients under treatment by a healthcare provider. The data includes selected portions of a subject's data (e.g., a patient's electronic medical record (EMR)) that describe aspects of the subject without compromising the confidentiality of the subject's identity. Access to the data is controlled by the collaboration networking tool 110. FIG. 3 provides additional detail about the manner in which data is stored in the data store 105.

A collaboration networking tool logic 110 controls access to the de-identified data in the data store 105. For example, the data from each provider may be individually password protected such that the collaboration networking tool 110 prevents access to data to seekers without the provider's password. The collaboration networking tool logic 110 receives de-identified data from a plurality of data providers (e.g., health care providers). The de-identified data is stored in the data store 105. The collaboration networking tool logic 110 is configured to provide prescribed types of access to authorized seekers (e.g., entities seeking to validate a protocol or recruit patients for clinical trial). In one embodiment, the collaboration networking tool logic 110 processes requests to query a given provider's data from a seeker. If the seeker is authorized to access the provider's data (e.g., has a password specific to the provider), the collaboration networking tool logic 110 allows the seeker to query the provider(s)' data.

In this manner, the collaboration networking tool logic 110 protects patient confidentiality and allows the data providers to maintain control over their data (e.g., by providing a password to the seeker) while providing access to a large pool of clinical data to seekers. The collaboration networking tool logic 110 may also include a billing feature that charges providers for maintaining their data in the data store 105 and seekers for accessing the data.

In one embodiment, the collaboration networking tool logic 110 and data store 105 are provided "in a cloud." In this embodiment, the data store 105 is physically located separately from the providers and seekers and is accessed by the providers and seekers via the internet. Providers and seekers may subscribe to a collaboration networking service that grants access to the data in the data store 105 by way of the collaboration networking tool logic 110. The data store 105 may be a dedicated, HIPAA certified data store that is maintained according to guidelines established by the providers.

Figure 2:
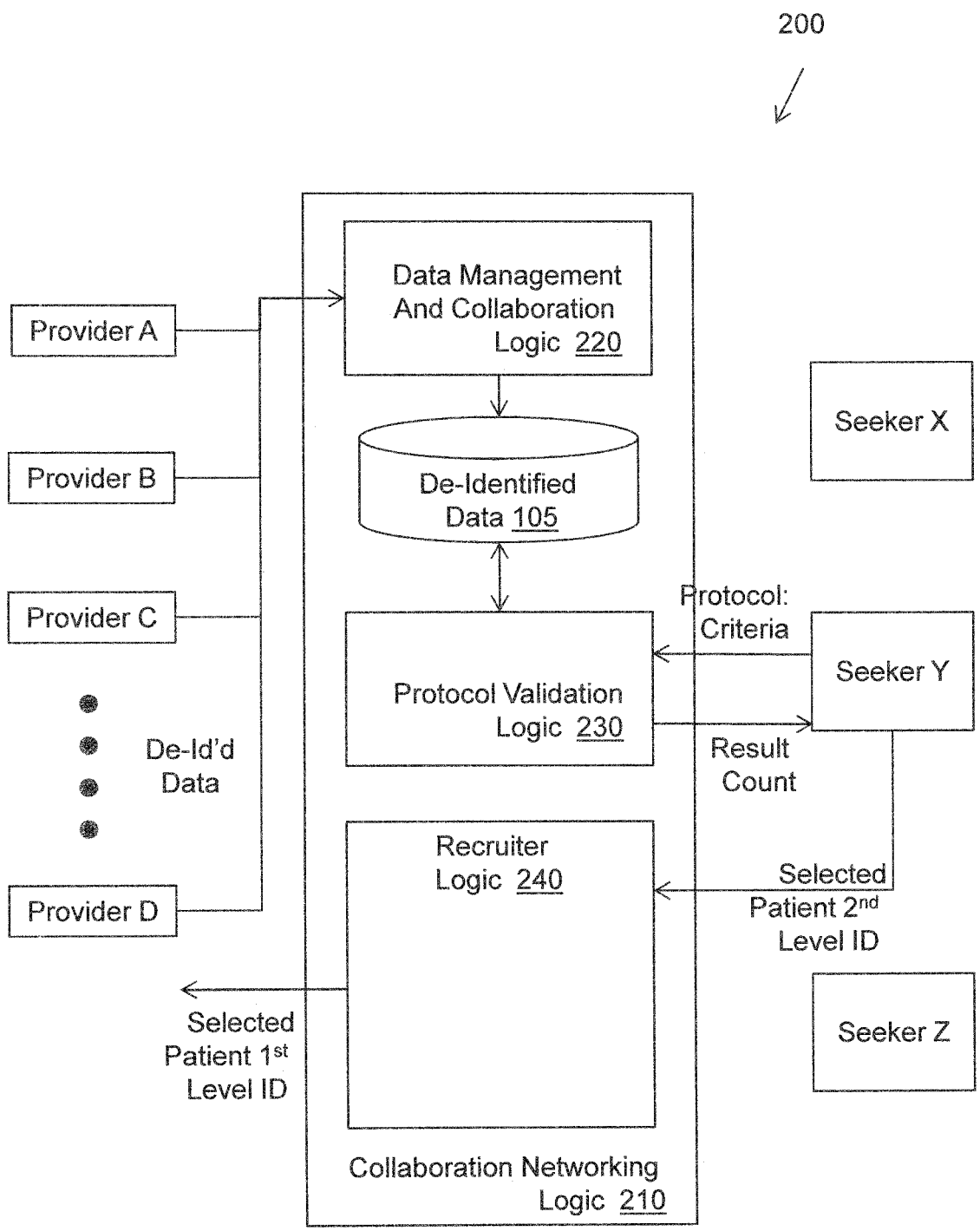
FIG. 2 illustrates another embodiment of a system associated with a collaboration networking tool.

FIG. 2 illustrates one example embodiment of a collaboration networking system 200 that includes a collaboration networking tool logic 210 and the de-identified data store 105. The collaboration networking tool logic 210 includes a data and collaboration management logic 220, a protocol validation logic 230, and a recruiter logic 240. The data and collaboration management logic 220 is configured to maintain the data in the data store 105. The data in the data store 105 is de-identified. Data maintained in the data store 105 may originate from EMRs, clinical data, laboratory data, pharmacy data, and schedule data. Prior to sending the data to the collaboration networking tool logic 210, providers remove all patient personally identifiable information (based on HIPAA regulations) and assign a unique first level masking identifier to each patients data. The providers retain a mapping of the first level masking identifiers to their original patient identifier. When the data arrives at the data and collaboration management logic 220, the data and collaboration management logic assigns a second level masking identifier to the data. The data and collaboration management logic 220 maintains a mapping of the second level masking identifiers to first level masking identifiers. In this manner the data is masked twice to protect patient privacy. In addition to patient identifiers, physician and treatment location identifiers may be masked.

In addition to the levels of masking, other measures may be taken to de-identify the data. For example, only selected attributes of a patient's data are stored in the data store 105. Columns of clinical data that contain physician notes may not be stored in the data store 105 to ensure that identifying details in notes are not inadvertently stored in the data store 105. Other security measures, as stipulated by HIPAA or other certifying entities, may also be taken. Data values that correspond to selected attributes may be converted to a predetermined format (e.g., standard medical terminology) to facilitate querying.

Providers may also be able to tag patients based on different levels of consent to clinical trial participation.

Thus, some patients may consent to give blood and tissue samples while not consenting to being contacted for clinical trials. Patients who are enrolled in studies may be tagged so they are not approached for recruitment by more than one study at a time. Tagging helps providers to efficiently recruit patients through their treating physicians wherever they are within the health system and provide a valuable service to the seekers.

FIG. 3 illustrates one embodiment of the data store 105. Data in the data store 105 is partitioned by provider so that data from different providers is not comingled and cannot be accessed by other providers. In one embodiment, the data for each provider is stored in a physically separate, dedicated database. A provider continues to "own" their data and may be given an opportunity to approve each instance of access to the provider's data in the data store 105. For example, each provider database may be protected by a password. Providers may authorize a seeker to access their database by giving the seeker a password. By default, seekers receive only patient counts and no line item detail when they query the data.

Incoming data from the providers is processed by an adaptor 310 that is configured for use by the specific provider's EMR system. The adaptor 310 selects the attributes that are to be stored in the data store 105 and applies formatting rules that translate the provider's specific formatting into the common formatting of the data store 105. The adaptor 310 replaces a first level masking identifier assigned by the provider with a second level masking identifier to the data as described above for double level masking. To keep the data store 105 up to date, the providers may push de-identified clinical data to the data store periodically. Of course, the more often the data is pushed, the more current the data store 105 is kept. In one embodiment, the data is pushed daily.

The embodiment of the data store 105 illustrated in FIG. 3 allows providers to maintain ownership of their patients' EMR data (e.g., by password protecting their data), and to stipulate in what manner the de-identified clinical data may be used. Because the data is made available to many seekers, the provider gains exposure for its patients to many possible clinical studies, raising the providers' stature with patients. In addition, the provider is able to access the data stored in the data store 105 in the predetermined format for its own purposes, possibly saving the cost of maintaining its own data store.

Returning to FIG. 2, the protocol validation logic 230 handles protocol validation queries from seekers. The seekers subscribe to a cloud based service that provides a tool for querying the data store 105. The protocol validation logic 230 is configured to process protocol validation queries on selected providers' data. The protocol validation queries specify one or more inclusion/exclusion criteria describing patients of interest to the seeker (e.g., possible candidates for a clinical trial). The collaboration networking tool 210 confirms authorization of the seeker with respect to the selected providers, for example by use of a password. If the seeker is authorized for the provider, the protocol validation logic returns a count of patients meeting the criteria.

Rather than returning the clinical data to the seeker, the collaboration networking tool logic 110 returns a count of patients that meet the criteria for each provider identifier. No "row level" information is provided in response to the protocol validation query. By evaluating this information, the seeker can readily identify which providers have patients that are suitable for their clinical study and how many patients each provider is treating. This allows a seeker to pursue a collaborative relationship with the identified providers to select specific patients. At no stage in the process does the seeker have any knowledge who the patients are because the data is de-identified. Only authorized personnel at the provider are able to identify the patients.

Figure 4:
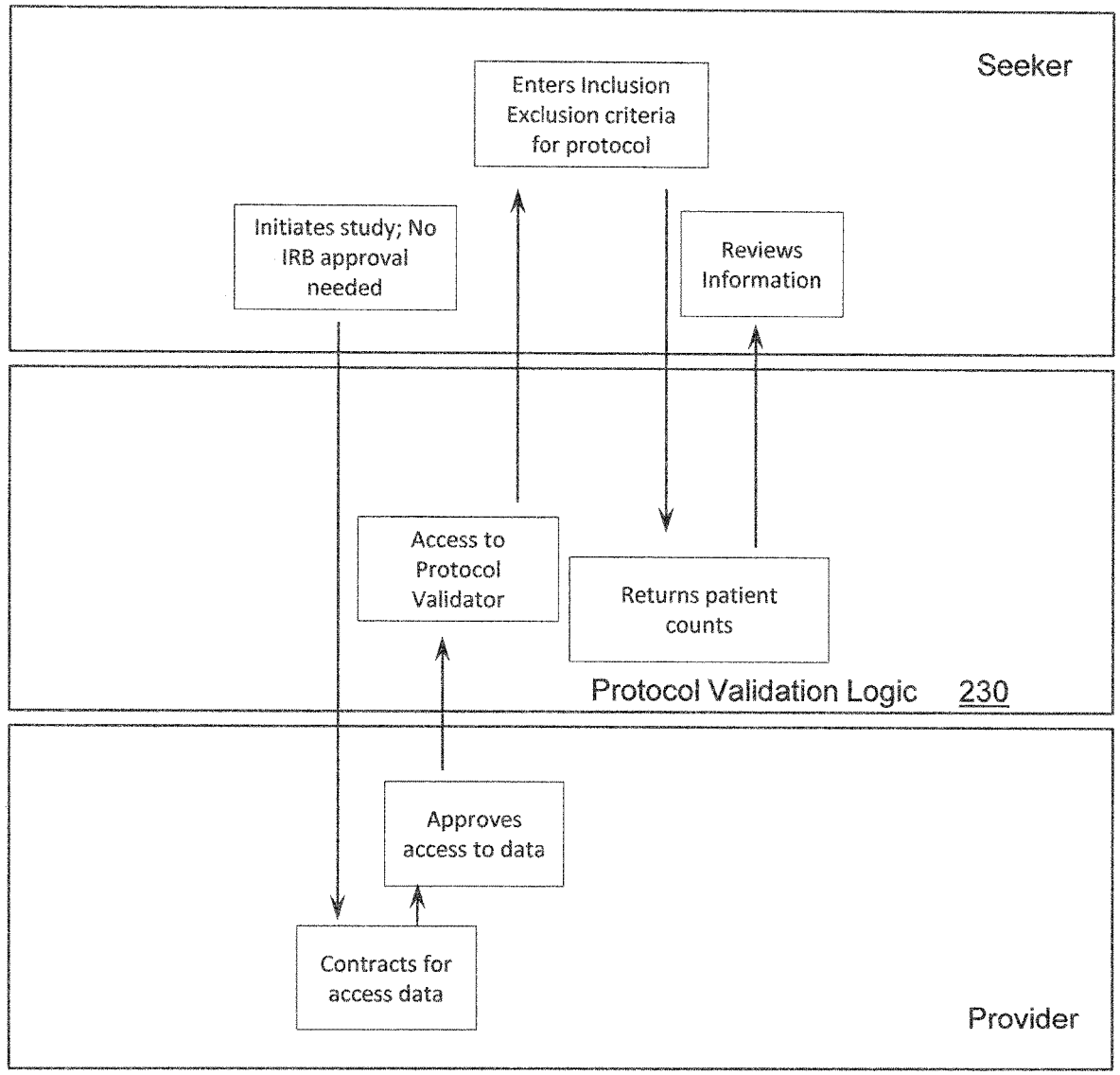
FIG. 4 illustrates another embodiment of a system associated with a collaboration networking tool.

FIG. 4 illustrates an example of how protocol validation queries are processed by one embodiment of the protocol validation logic 230. At the start, the seeker subscribes to the collaboration networking service and initiates a study to locate patients under treatment by specified providers for participation in clinical study. Because all the processes of the protocol validation logic can be approved by the provider when access (e.g. password) is granted to the seeker, no Internal Review Board (IRB) approval is necessary. The protocol validation logic 230 allows querying of a provider's data by the seeker if the seeker has been authorized by the provider.

If the provider authorizes the querying by the seeker, the provider uses the collaboration networking tool to grant access to data to the seeker and thus approves the protocol validation logic's access to the data. The seeker enters a protocol validation query that has inclusion/exclusion criteria for the clinical study. The protocol validation logic 230 accesses the provider's de-identified clinical data in the data store 105. The query returns a count of patients who meet the criteria. The seeker then reviews this information and decides whether to collaborate with the provider in the clinical study.

Returning to FIG. 2, the recruiter logic 240 is configured to facilitate collaboration between the seekers and providers while protecting patient confidentiality. In one embodiment, the recruiter logic 240 mediates communication between the seeker and provider by translating the second identifier for a patient referenced a communication from the seeker to the first identifier that is recognizable by the provider.

Figure 5:
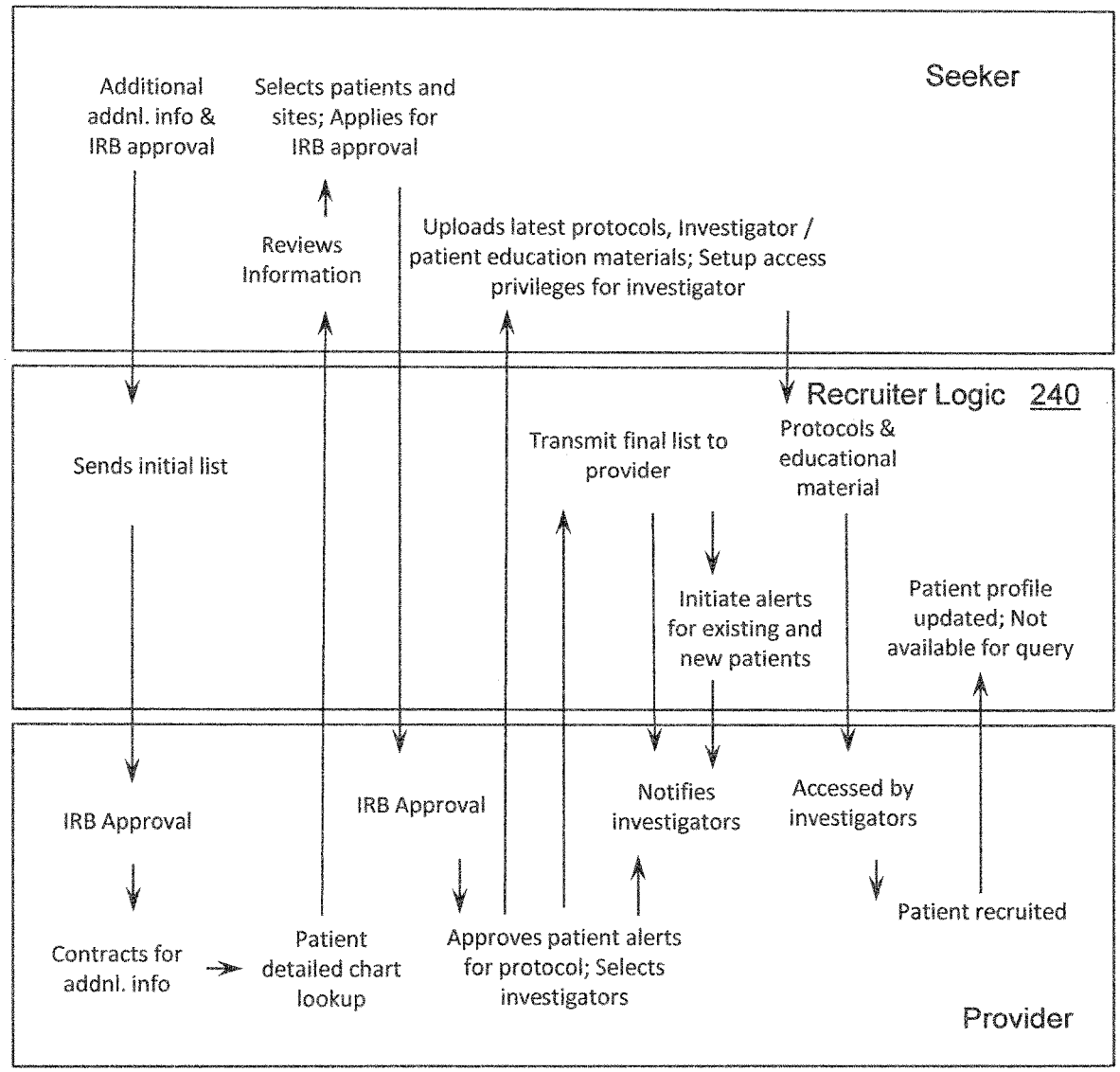
FIG. 5 illustrates another embodiment of a system associated with a collaboration networking tool.

FIG. 5 illustrates how data is processed by one embodiment of the recruiter logic 240 during collaboration between a seeker and a provider to perform a clinical study. Recalling FIG. 4, the seeker has a list of second level masking identifiers for patients that meet the inclusion/exclusion criteria of the protocol validation query. To begin a collaborative relationship with a selected provider, IRB approval may be required. The list of patients (as identified by the second identifier assigned by the collaboration networking tool logic) is sent to the recruiter logic 240. The recruiter logic substitutes the second level masking identifier with the first level masking identifier and transmits the list to the provider. After IRB approval at the provider, the provider may provide the seeker additional information on the selected patients.

The seeker uses the information to select patients for the study and transmits the list of selected patients and a request for IRB approval to the recruiter logic 240. The recruiter logic substitutes first level masking identifiers for second level masking identifiers in the list and provides the list to the provider for IRB approval. The provider selects investigators (physicians or nurses who will be administering the protocol to the patients. The seeker uploads the protocols and education materials to the patient recruiter 240 and sets up access privileges to these materials for the investigators. Alerts concerning the protocol are initiated for existing and new patients and investigators are notified by the alerts to changes in the protocol. During the clinical study, the protocols and educational materials are accessed by the investigators to determine how to treat the various patients and to record the results of the trial. The patient recruiter 240 continues to identify patients by the second identifier for the seeker and by the first identifier for the provider, maintaining the confidentiality of the patients. Once a patient has been recruited for a clinical trial, the patient's clinical data in the data store (not shown) may be tagged for a predetermined time period to indicate that the patient's data should not be returned as a result to any other protocol validation queries.

Figure 6:
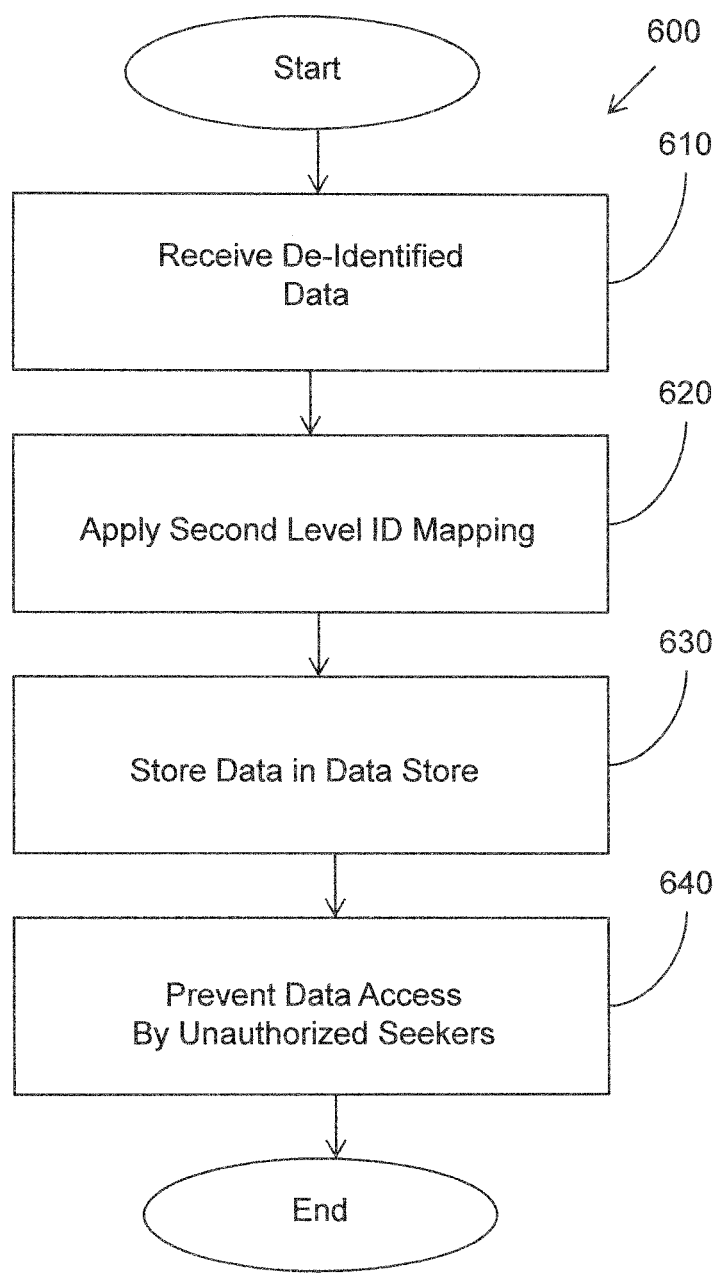
FIG. 6 illustrates an embodiment of a method associated with a collaboration networking tool.

FIG. 6 outlines one embodiment of a method 600 associated with a collaboration networking tool. At 610, the method includes receiving, from a provider, de-identified data that describes a given subject (e.g., patient). The de-identified data includes a first level masking identifier assigned to the given subject by the provider. At 620, the method includes associating a second level masking identifier to the data. At 630, the method includes storing the de-identified data in a data store. At 640, the method includes preventing access to the data by unauthorized seekers. In one embodiment, preventing access is performed by requiring a provider specified password prior to allowing access to the provider's data.

The method may also include processing protocol validation queries. Protocol validation queries include a protocol's inclusion/exclusion criteria. In response to the protocol validation queries, the counts of subjects whose de-identified data that meet query selection criteria are returned rather than the de-identified data itself. This means that de-identified data is not returned in response to protocol validation queries on the data store.

In some embodiments, the method also includes removing the first level masking identifier from the de-identified data prior to storing the de-identified data in the data store. The method assigns a second level masking identifier to the de-identified data and stores the second level masking identifier with the de-identified data in the data store. A mapping of the first level masking identifier to the second level masking identifier is maintained for use in future processing.

In one embodiment, the method 600 includes receiving second level masking identifiers from a seeker. First level masking identifiers associated with the identified patients are provided to the provider of the data.

In one embodiment, the method 600 includes screening the received data by selecting predetermined de-identified data attribute values and storing the selected data attribute values in the data store without storing de-identified data not corresponding to a predetermined data attribute value.

Figure 7:
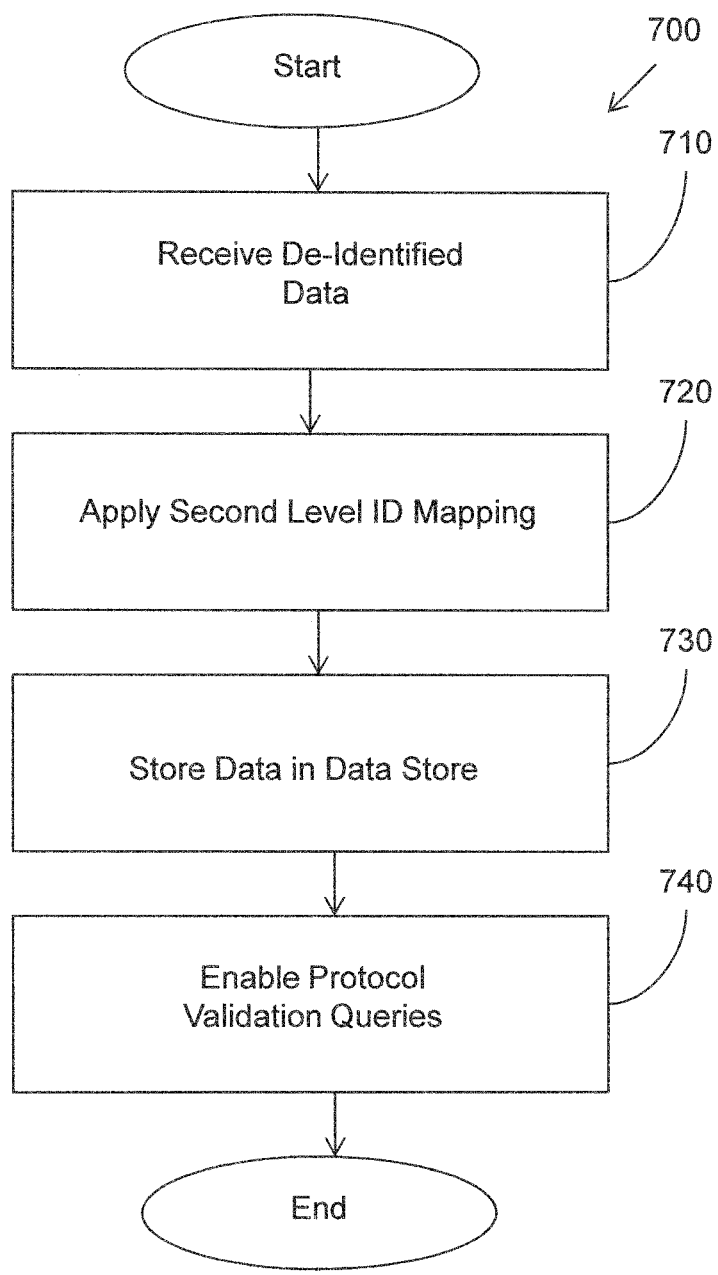
FIG. 7 illustrates another embodiment of a method associated a collaboration networking tool.

FIG. 7 outlines one embodiment of a method 700 associated with a collaboration networking tool. At 710, the method includes receiving, from a provider, de-identified data that describes a given subject (e.g., patient). The de-identified data includes a first level masking identifier assigned to the given subject by the provider. At 720, the method includes associating a second level masking identifier corresponding with the de-identified data. At 730, the method includes storing the de-identified data in a data store. At 740, the method includes enabling protocol validation queries on the de-identified data in the data store. Protocol validation queries include a protocol's inclusion/exclusion criteria. In response to the protocol validation queries, counts of subjects whose data (e.g., clinical data) meet query selection criteria are returned rather than the subjects' data. This means that de-identified data is not returned in response to protocol validation queries on the data store.

Figure 8:
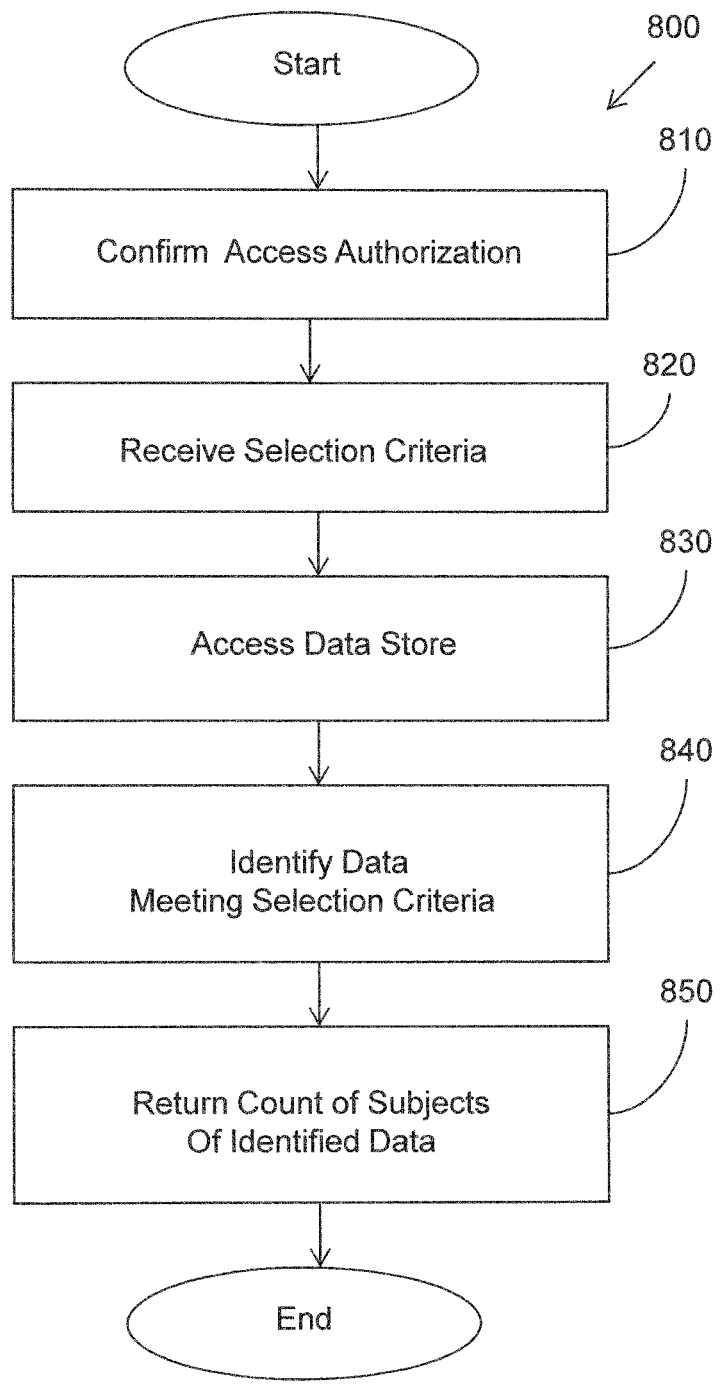
FIG. 8 illustrates another embodiment of a method associated a collaboration networking tool.

FIG. 8 illustrates one embodiment of a method 800 associated with collaboration networking. At 810, the method includes confirming that a seeker has access to a selected provider's data. For example, the method may include determining the validity of a password prior to proceeding. At 820, the method includes receiving, from a seeker, a protocol validation query specifying one or more selection criteria (e.g., inclusion/exclusion criteria). At 830, the method includes accessing a data store that stores data associated with a plurality of subjects. The method includes, at 840, identifying subjects in the data store that meet the criteria. At 850, the method includes returning, to the seeker, a count of subjects having data that meets the criteria.

In some embodiments, the method 800 allows for collaboration between the seeker and provider. To this end, the method includes receiving, from the seeker, a selected second level masking identifier. The method includes retrieving a corresponding first level masking identifier and providing the first level masking identifier to the provider. In this way the method allows for the seeker and provider to communicate regarding a particular patient without exchanging any identifying data.

General Computer Embodiment

Figure 9:
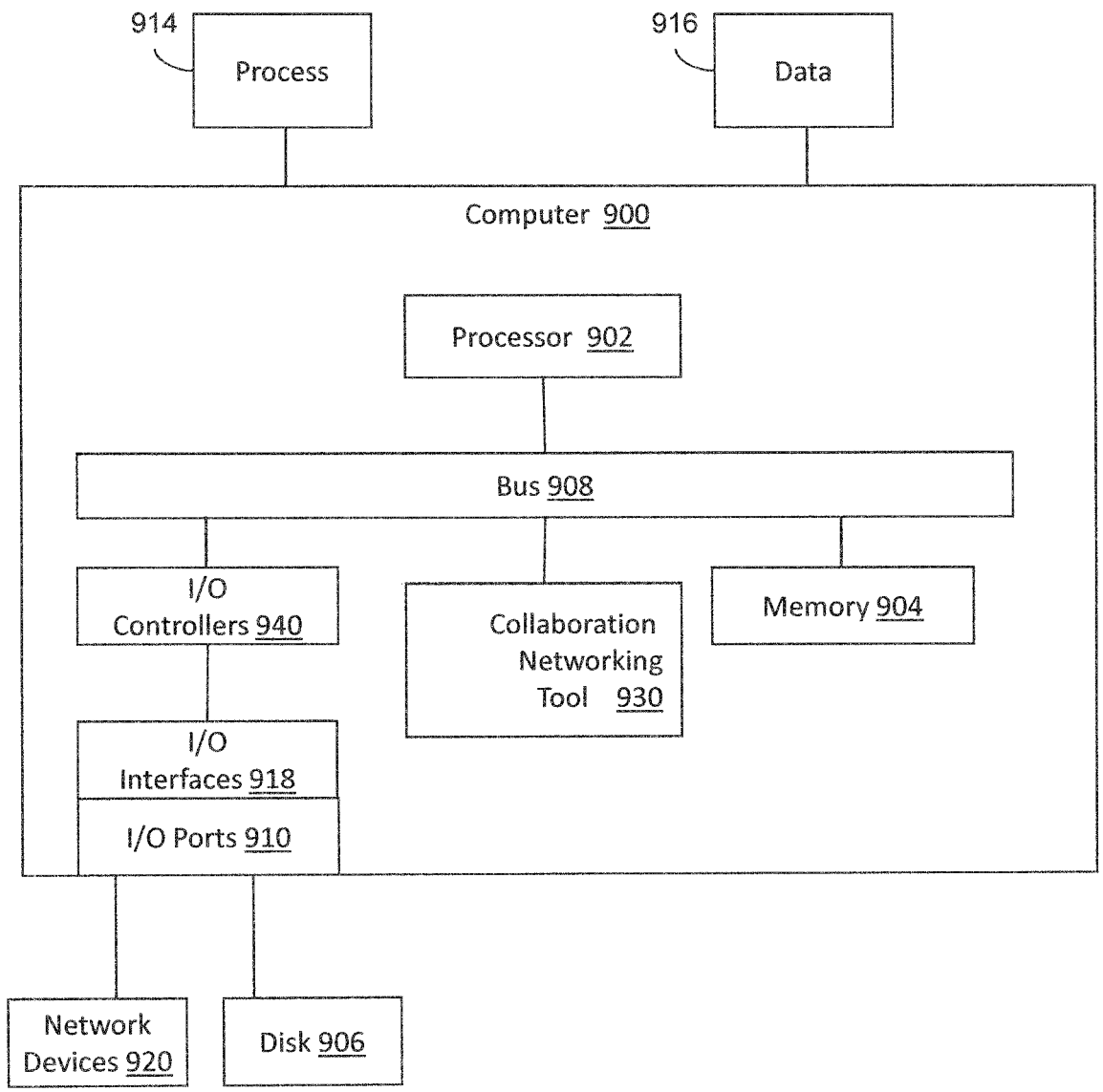
FIG. 9 illustrates an embodiment of a computing system in which example systems and methods, and equivalents, may operate.

FIG. 9 illustrates an example computing device in which example systems and methods described herein, and equivalents, may operate. The example computing device may be a computer 900 that includes a processor 902, a memory 904, and input/output ports 910 operably connected by a bus 909. In one example, the computer 900 may include a collaboration networking tool 930 configured to store de-identified data in manner that facilitates collaboration between providers of the data and seekers of subjects while maintaining confidentiality of the subjects and ownership of data by providers of the data. In different examples, the tool 930 may be implemented in hardware, a non-transitory computer-readable medium with stored instructions, firmware, and/or combinations thereof. While the tool 930 is illustrated as a hardware component attached to the bus 908, it is to be appreciated that in one example, the tool 930 could be implemented in the processor 902.

In one embodiment, the collaboration networking tool 930 is a means (e.g., hardware, non-transitory computer-readable medium, firmware) for storing de-identified data in manner that facilitates collaboration between providers of the data and seekers of subjects while maintaining confidentiality of the subjects and ownership of data by providers of the data.

The means may be implemented, for example, as an ASIC programmed to support querying on de-identified data. The means may also be implemented as stored computer executable instructions that are presented to computer 900 as data 916 that are temporarily stored in memory 904 and then executed by processor 902.

Generally describing an example configuration of the computer 900, the processor 902 may be a variety of various processors including dual microprocessor and other multiprocessor architectures. A memory 904 may include volatile memory and/or non-volatile memory. Non-volatile memory may include, for example, ROM, PROM, and so on. Volatile memory may include, for example, RAM, SRAM, DRAM, and so on.

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a Zip drive, a flash memory card, a memory stick, and so on. Furthermore, the disk 906 may be a CD-ROM drive, a CD-R drive, a CD-RW drive, a DVD ROM, and so on. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output devices via the i/o interfaces 918 and the input/output ports 910. Input/output devices may be, for example, a keyboard, a microphone, a pointing and selection device, cameras, video cards, displays, the disk 906, the network devices 920, and so on. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the methods described in FIGS. 6-8.

While for purposes of simplicity of explanation, the illustrated methodologies in the figures are shown and described as a series of blocks, it is to be appreciated that the methodologies are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.
ROM: read only memory.
PROM: programmable ROM.
EPROM: erasable PROM.
EEPROM: electrically erasable PROM.
SQL: structured query language.
OQL: object query language.
USB: universal serial bus.
XML: extensible markup language.
WAN: wide area network.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

In some examples, "database" is used to refer to a table. In other examples, "database" may be used to refer to a set of tables. In still other examples, "database" may refer to a set of data stores and methods for accessing and/or manipulating those data stores.

"Data store", as used herein, refers to a physical and/or logical entity that can store data on a non-transitory computer readable medium. A data store may be, for example, a database, a table, a file, a list, a queue, a heap, a memory, a register, and so on. In different examples, a data store may reside in one logical and/or physical entity and/or may be distributed between two or more logical and/or physical entities.

"Logic", as used herein, includes but is not limited to hardware, firmware, a non-transitory computer readable medium that stores instructions, instructions in execution on a machine, and/or combinations of each to perform a function(s) or an action(s), and/or to cause a function or action from another logic, method, and/or system. Logic may include a microprocessor, a discrete logic (e.g., ASIC), an analog circuit, a digital circuit, a programmed logic device, a memory device containing instructions, and so on. Logic may include one or more gates, combinations of gates, or other circuit components. Where multiple logics are described, it may be possible to incorporate the multiple logics into one physical logic. Similarly, where a single logic is described, it may be possible to distribute that single logic between multiple physical logics.

"Query", as used herein, refers to a semantic construction that facilitates gathering and processing information. A query may be formulated in a database query language (e.g., SQL), an OQL, a natural language, and so on.

"User", as used herein, includes but is not limited to one or more persons, computers or other devices, or combinations of these.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is used herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be used.

What is claimed is:

1. A non-transitory computer-readable medium storing computer-executable instructions that when executed by a processor of a computer cause the computer to:
in response to receiving, from a provider device, electronic de-identified records, store the electronic de-identified records in a database, wherein each de-identified record comprises de-identified data describing characteristics of a subject without identifying the subject, wherein the de-identified records include a first level masking identifier for masking portions of the de-identified records;
assign, by at least the processor, a second level masking identifier to the de-identified data and generate a mapping that maps the second level masking identifier to the first level masking identifier;
receive, via an internet communication from a seeker device, a request to access the de-identified records;
determine, by at least the processor, whether the provider device of the de-identified data authorizes the seeker device to access the de-identified records;
in response to determining that the seeker device is authorized, receiving, from the seeker device, one or more selection criteria, and in response cause the processor to;
access the database that stores the de-identified records;
identify subjects having a de-identified record in the database that meets the one or more selection criteria; and
return, to the seeker device, an internet communication that communicates a count of identified subjects;
in response to receiving, via an internet communication from the seeker device, a masking identifier that identifies a subject and a request for information about the subject, causing at least the processor to:
access the mapping of the second level masking identifiers to the first level masking identifiers to translate the masking identifier into a first level masking identifier that was assigned to the subject by the provider; and
communicate, from the computer via an internet communication, the request and the first level masking identifier to the provider device without communicating the second level masking identifier to the provider device,
wherein the first level masking identifier and the second level masking identifier cause no identifying information about the subject to be exchanged in the internet communication from the computer between the seeker device and the provider device.

2. The non-transitory computer-readable medium of claim 1, further comprising instructions that cause the computer to determine whether the seeker device is authorized by receiving a password from the seeker device and comparing the password to a password from the provider device.

3. The non-transitory computer-readable medium of claim 1, where the instructions further comprise instructions that cause the computer to:
create the de-identified records by, for each de-identified record:
receiving, from the provider device, a record that includes the first level masking identifier assigned to the subject by the provider device, where the provider device retains a first mapping between the first level masking identifier and a subject identifier that uniquely identifies the subject, where the received record does not include the subject identifier;
assigning the second level masking identifier to the subject;
maintaining a second mapping of the first level masking identifier to the second level masking identifier;
removing the first level masking identifier from the record; and
adding the second level masking identifier to the record to create the de-identified record.

4. A computing system, comprising:
a processor;
a database that stores electronic de-identified records associated with a plurality of subjects, where each de-identified record comprises de-identified data describing characteristics of a subject without identifying the subject, wherein the de-identified records include a first level masking identifier for masking portions of the de-identified records;
wherein the processor is configured to (i) assign a second level masking identifier to the de-identified data of each of the de-identified records and (ii) generate a mapping that maps the second level masking identifier to the first level masking identifier for the de-identified records;
a protocol validation logic configured to cause the processor to:
receive, via an internet communication from a seeker device, one or more selection criteria for selecting de-identified records;
access the data store and search for de-identified records that meet the one or more selection criteria;
count a number of subjects having a de-identified record that meets the one or more selection criteria;
return, to the seeker via an internet communication, the count of number of subjects whose de-identified records meet the one or more selection criteria; and
recruiter logic configured to cause the processor to mediate communication between the provider device and the seeker device to protect data communications, wherein in response to receiving, via an internet communication from the seeker device, (i) a requested masking identifier that is a second level masking identifier that identifies a subject and (ii) a request for information about the subject, the recruiter logic is configured to cause the processor to:
   translate, using the mapping, the second level masking identifier into a first level masking identifier that was assigned to the subject by the provider device; and
   communicate the request and the first level masking identifier to the provider device via an internet communication without communicating the second level masking identifier to the provider,
   wherein no identifying information about the subject is exchanged in the internet communication between the seeker device and the provider device.

5. The computing system of claim 4, where the provider device has custody of identifying information associated with the de-identified records, the system further comprising a data and collaboration management logic configured to cause the processor to:
   determine whether the seeker device has access to the de-identified records by receiving a password from the seeker device and comparing the password to a password from the provider device; and
   decline to access the data store when the password from the seeker device does not match the password from the provider device.

6. The computing system of claim 5 where the recruiter logic is further configured to cause the processor to:
   create the de-identified records by, for each de-identified record:
      receiving, from the provider device, a record that includes a first level masking identifier assigned to the subject by the provider device, where the provider device retains a first mapping between the first level masking identifier and a subject identifier that uniquely identifies the subject, where the received record does not include the subject identifier;
      assigning a second level masking identifier to the subject;
      maintaining a second mapping of the first level masking identifier to the second level masking identifier;
      removing the first level masking identifier from the record; and
      adding the second level masking identifier to the record to create a de-identified record.

7. A computer-implemented method, comprising:
   storing electronic de-identified records in a database, where each de-identified record includes i) de-identified data describing characteristics of a subject ii) a first level masking identifier for the subject for masking portions of the de-identified record;
   assign, by at least the processor, a second level masking identifier to the de-identified data of each de-identified record, and generate a mapping that maps the second level masking identifier to the first level masking identifier;
   storing the mapping of the second level masking identifiers to the first level masking identifiers;
   controlling access to identifying information in the database comprising:
      in response to a request via an internet communication from a seeker device requesting data about a subject wherein the request includes the second level masking identifier:
      translating, using the mapping, the second level masking identifier into a first level masking identifier for the subject;
      substituting the second level masking identifier with the first level masking identifier in the request;
      communicating the request with the substituted first level masking identifier to the provider device via an internet connection,
      such that no identifying information about the subject is exchanged between the seeker device and the provider device by way of the internet connection.

* * * * *